US010105516B2

(12) United States Patent
Selkee

(10) Patent No.: US 10,105,516 B2
(45) Date of Patent: *Oct. 23, 2018

(54) CATHETER WITH IMPROVED TORQUE TRANSMISSION

(71) Applicant: BIOSENSE WEBSTER (ISRAEL) LTD., Yokneam (IL)

(72) Inventor: Thomas V. Selkee, Claremont, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/011,393

(22) Filed: Jan. 29, 2016

(65) Prior Publication Data

US 2016/0144153 A1 May 26, 2016

Related U.S. Application Data

(63) Continuation of application No. 13/677,228, filed on Nov. 14, 2012, now Pat. No. 9,248,255.

(51) Int. Cl.
*A61M 31/00* (2006.01)
*A61M 25/01* (2006.01)
(Continued)

(52) U.S. Cl.
CPC ..... *A61M 25/0147* (2013.01); *A61B 18/1492* (2013.01); *A61M 25/0053* (2013.01);
(Continued)

(58) Field of Classification Search
CPC ...... A61B 18/1492; A61B 2018/00839; A61B 2218/002; A61M 25/0054; A61M 25/0147
(Continued)

(56) References Cited

U.S. PATENT DOCUMENTS

| RE34,502 E | 1/1994 | Webster, Jr. |
| 5,341,818 A | 8/1994 | Abrams et al. |

(Continued)

FOREIGN PATENT DOCUMENTS

| CN | 103181819 A | 7/2013 |
| CN | 103284786 A | 9/2013 |
| CN | 103347560 A | 10/2013 |
| CN | 103356281 A | 10/2013 |
| JP | H07-505554 A | 6/1995 |
| JP | 2006255401 A | 9/2006 |

(Continued)

OTHER PUBLICATIONS

European search report dated Feb. 6, 2014 for European Patent Application No. 13192744.4, 8 pages.

*Primary Examiner* — Emily Schmidt
*Assistant Examiner* — Tiffany Legette-Thompson
(74) *Attorney, Agent, or Firm* — Roberts Mlotkowski Safran Cole & Calderon, P.C.

(57) ABSTRACT

A catheter has a deflection beam and a single continuous puller wire to effectuate bi-directional deflection. A joint between a catheter body and a deflectable distal section effectively transmits torque from a control handle. The joint includes two open-shaped brackets, each affixed to a respective side of the flat deflection beam to form a closed-shaped hollow body that bridges and circumferentially encircles the beam. Each bracket has through-holes into which thermoplastic material of the catheter body and the deflectable distal section can melt and migrate to form interlocking nodes.

20 Claims, 11 Drawing Sheets

(51) Int. Cl.
*A61B 18/14* (2006.01)
*A61M 25/00* (2006.01)
*A61B 18/00* (2006.01)
*A61B 34/20* (2016.01)
*A61B 5/042* (2006.01)

(52) U.S. Cl.
CPC .... *A61M 25/0138* (2013.01); *A61M 25/0141* (2013.01); *A61M 25/0144* (2013.01); *A61B 5/042* (2013.01); *A61B 2018/00577* (2013.01); *A61B 2018/00839* (2013.01); *A61B 2034/2051* (2016.02); *A61B 2218/002* (2013.01); *A61M 25/0009* (2013.01); *A61M 25/0051* (2013.01); *A61M 25/0052* (2013.01); *A61M 2025/015* (2013.01)

(58) Field of Classification Search
USPC .................................. 604/95.04, 525, 93.01
See application file for complete search history.

(56) References Cited

U.S. PATENT DOCUMENTS

| | | | |
|---|---|---|---|
| 5,480,382 | A | 1/1996 | Hammerslag et al. |
| 5,569,218 | A | 10/1996 | Berg |
| 7,618,379 | B2 | 11/2009 | Reynolds et al. |
| 7,731,669 | B2 | 6/2010 | Mathews et al. |
| 2002/0165461 | A1* | 11/2002 | Hayzelden ......... A61B 18/1492 600/523 |
| 2003/0181855 | A1* | 9/2003 | Simpson ........... A61M 25/0041 604/95.04 |
| 2008/0097395 | A1 | 4/2008 | Adams et al. |
| 2012/0203169 | A1 | 8/2012 | Tegg |

FOREIGN PATENT DOCUMENTS

| | | |
|---|---|---|
| JP | 2012050855 A | 3/2012 |
| JP | 2012115426 A | 6/2012 |
| WO | 02089895 A2 | 11/2002 |

* cited by examiner

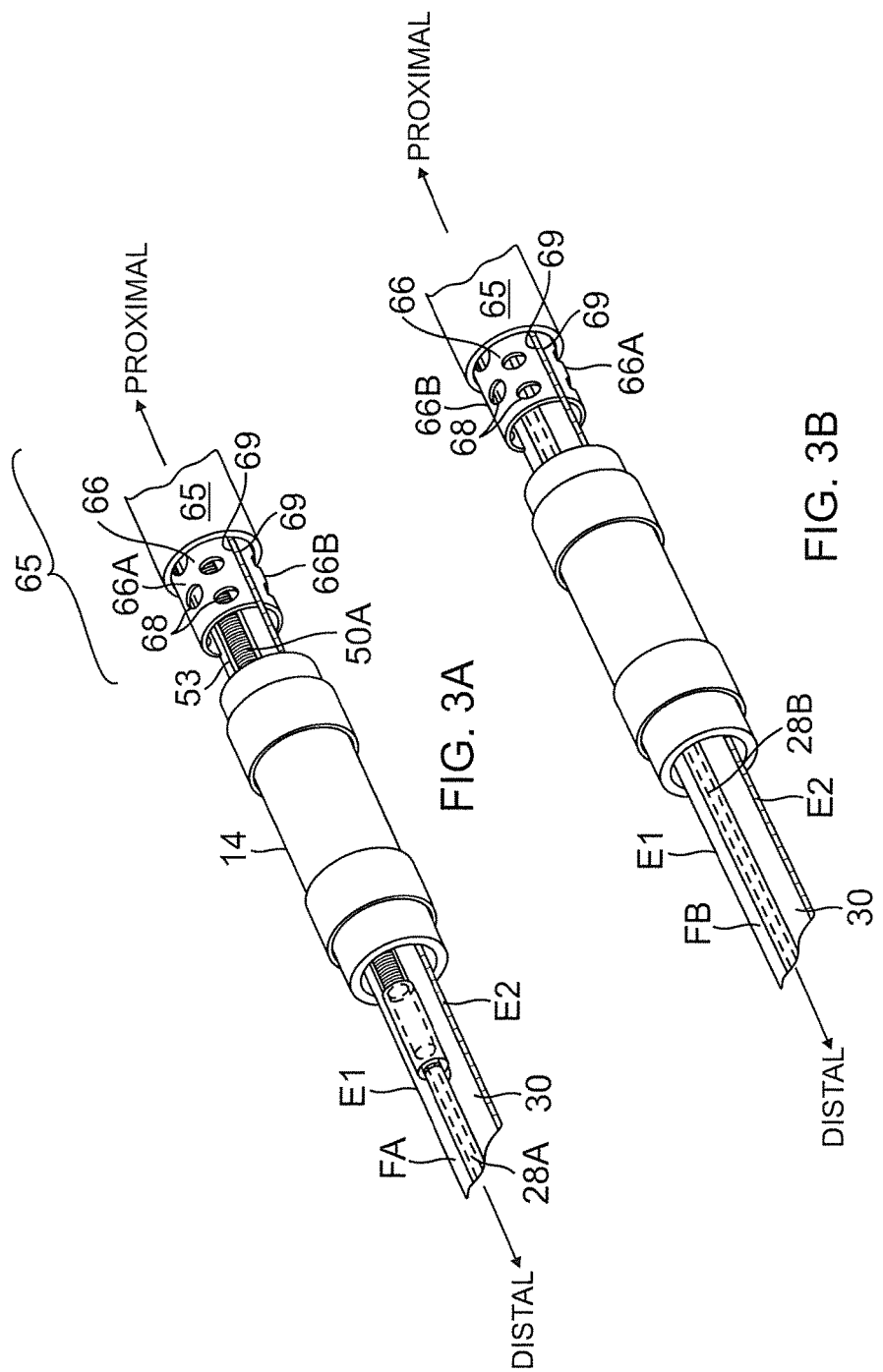

CATHETER WITH IMPROVED TORQUE TRANSMISSION

CROSS-REFERENCE TO RELATED APPLICATION(S)

This application is a continuation of and claims priority to and the benefit of U.S. patent application Ser. No. 13/677,228 filed Nov. 14, 2012, now U.S. Pat. No. 9,248,255, the entire content of which is incorporated herein by reference.

FIELD OF INVENTION

The present invention relates to a medical device for use in the vessel of a patient for the purpose of diagnosing or treating the patient, such as mapping tissue and/or ablating tissue using radio frequency (RF) or other sources of energy. More particularly, the invention relates to a longer deflectable catheter having a flat beam for on-plane bi-directional deflection with improved torque transmission, and method of making same.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Catheters adapted for on-plane bi-directional deflection are also known. A flat beam is normally provided to enable deflection on both sides of the beam within a plane. However, the puller wire in tension under deflection often flips over to the other side of the beam, or where the puller wires are located close to the beam, a large bending moment is required to deflect the beam, imposing significant stress on the puller wires. Moreover, with the puller wires close and tightly constrained to the beam, adhesion failure or rupture of the constraint poses a risk.

The employment of a pair of puller wires to effectuate bi-directional deflection also required a number of components which occupied space in a space-constrained catheter. More components also increased the risk of component failures. The use of T-bars and/or crimps can unduly fatigue puller wires and impart shear stresses resulting from skewed or off axis alignment of puller wires relative to the longitudinal axis of the catheter, even if by a minor degree. While bi-directional deflection is unquestionably an improvement over uni-directional deflection, bi-directional deflection is typically symmetrical whereas many regions of the heart lack symmetry. Thus, it would be desirable to provide a catheter with more deflection variety and options.

With catheters that have long deflectable tip designs (e.g., 90-180 mm or longer) that utilize a flat deflection beam as part of the tip steering mechanism, there is a need to provide a transition between the catheter shaft and the deflectable tip that transfers torsional forces from the control handle to the tip with high fidelity and low hysteresis, to provide the physician or user the ability to accurately place and control the tip deflection within the patient.

Accordingly, a need exists for a catheter with long deflectable tip designs using a deflectable beam capable of predictable on-plane bi-directional deflection (symmetrical and nonsymmetrical) which employs a flat deflection beam which can be deflected easily without significant tensile or shear stress on the puller wires and provides a transition between the catheter body and deflectable tip that can transmit torque from the control handle to the deflectable tip.

SUMMARY OF THE INVENTION

The present invention is directed to a catheter having a deflection beam and a single continuous puller wire to effectuate bi-directional deflection with less deflection components for reducing catheter size without compromising functionality, including the ability to carry, house and support mapping and/or ablation components, such as a multitude of electrodes and lead wires. In one embodiment, the catheter has a catheter body and a distal section with a flat deflection beam, and a single continuous puller wire that extends from a control handle, up along the catheter body and one side of the beam, and U-bends around a distal end of the flat beam. The puller wire then runs back down along the other side of the flat beam, down the catheter body and back into the control handle. The catheter advantageously provides a joint between the catheter body and the distal section that is particularly effective in transmitting torque from the control handle to the catheter body and the distal section. Each of the catheter body and the distal section has a tubular structure with a central lumen. Each tubular structure has at least an inner layer of a thermoplastic material. The joint includes two open-shaped brackets, each of which is affixed to a respective side of the flat deflection beam so as to face other and form a closed-shaped hollow body that bridges and circumferentially encircles the beam at the joint while allowing components to pass through the joint uninterrupted. A distal end of the catheter body is slipped on a proximal end of the hollow body and a proximal end of the deflectable section is slipped on a distal end of the hollow body. Each bracket has recesses or through-holes into which the thermoplastic material of each tubular structure can melt and migrate to form interlocking nodes with the application of heat and pressure, for example, by utilizing a two piece thermal fusing die. A heat shrink tubing may be placed over the joint during heat fusion and removed after cooling.

In a more detailed embodiment, each bracket has a half cylindrical shape with a "C" cross-section along its length and two longitudinal side edges. Affixed to opposite of the flat beam along the side edges, a pair of bracket forms a hollow cylindrical body around the beam at the joint. The brackets are constructed of any suitable materials, including full hard, cold worked stainless steel alloys (304 or 316 full hard condition), nickel/titanium alloys (nitinol) or phosphor bronze alloys They may be coated with adhesive for better bonding with the thermoplastic material of the tubular structures.

In another more detailed embodiment, each tubular structure also has a layer of braided mesh over the thermoplastic material, and an outer layer of an elastomeric material.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 3A is a perspective view of an interior of a deflectable section, including one side of a deflection beam.

FIG. 3B is a perspective view of the interior of the deflectable section of FIG. 3A, including the other side of the deflection beam.

DETAILED DESCRIPTION OF THE INVENTION

Figure 1:
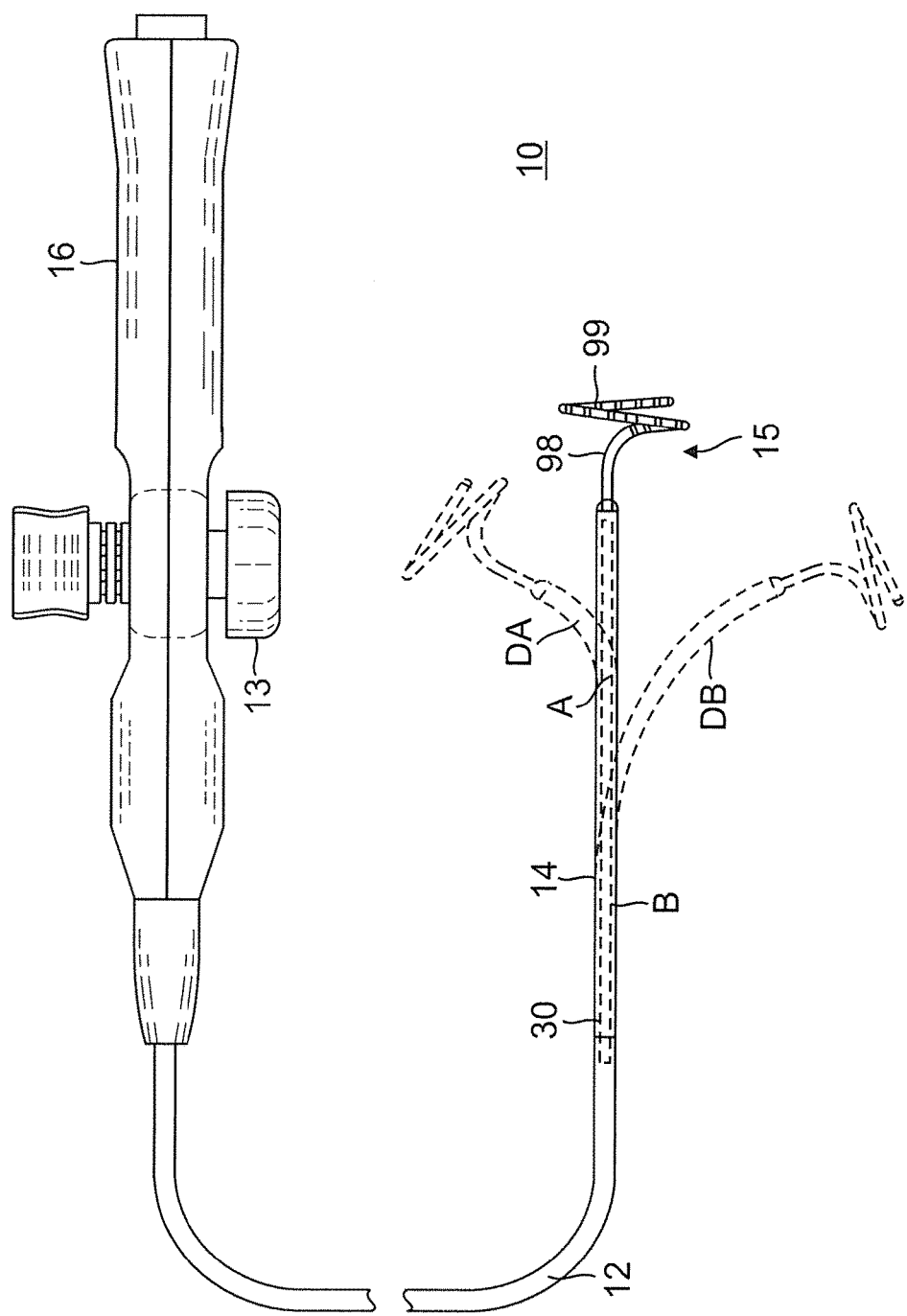
FIG. 1 is a top plan view of a catheter in accordance with one embodiment of the present invention.

The present invention is directed to a catheter having a catheter shaft and a deflectable distal portion having an elongated flat beam or "blade" to effectuate bi-directional deflection while maximizing space within the catheter for components including lead wires, puller wires, cables, tubings and any other support members for advanced distal dip designs. With reference to FIG. 1, a catheter 10 in accordance with an embodiment of the present invention includes a catheter shaft 12, a deflectable distal section 14 distal of the catheter shaft, and a control handle 16 proximal of the catheter shaft. The deflectable section 14 has a tip assembly 15 having, for example, a lasso design with a generally circular main portion extending and oriented transversely from a distal end of the deflectable section 14. Advantageously, the deflectable section 14 supporting the tip assembly 15 is configured for nonsymmetrical bi-directional deflection with one curvature or deflection DA on one side of the catheter and another curvature or deflection DB on the other side. Deflection is effectuated by user manipulation of an actuator 13 provided on the control handle 16 which moves a puller wire that extends along the catheter from the control handle 16, through the catheter body and into the distal section 14.

Figure 2:
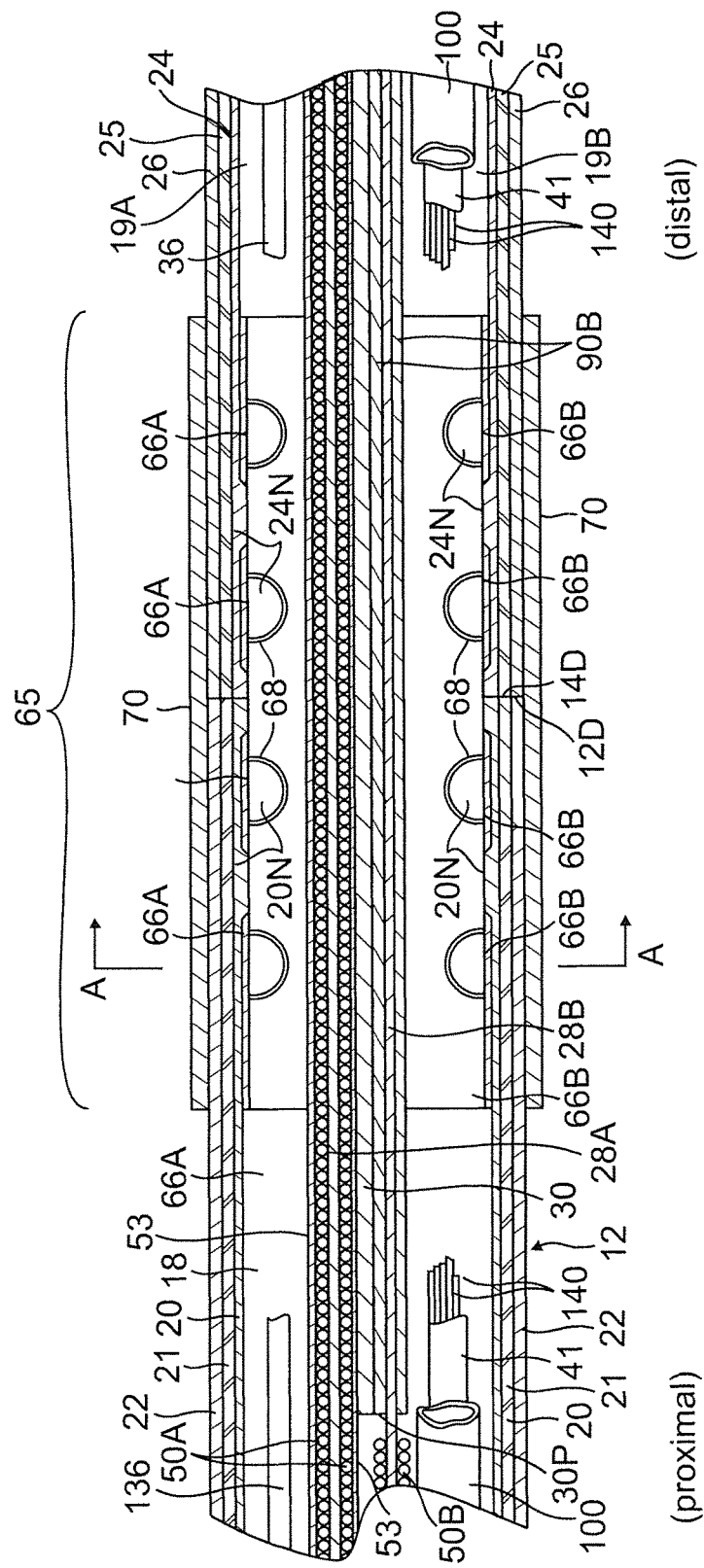
FIG. 2 is a side cross-sectional view of a transition section between a catheter body and a deflectable section of the catheter of FIG. 1 in accordance with one embodiment of the present invention.
Figure 2A:
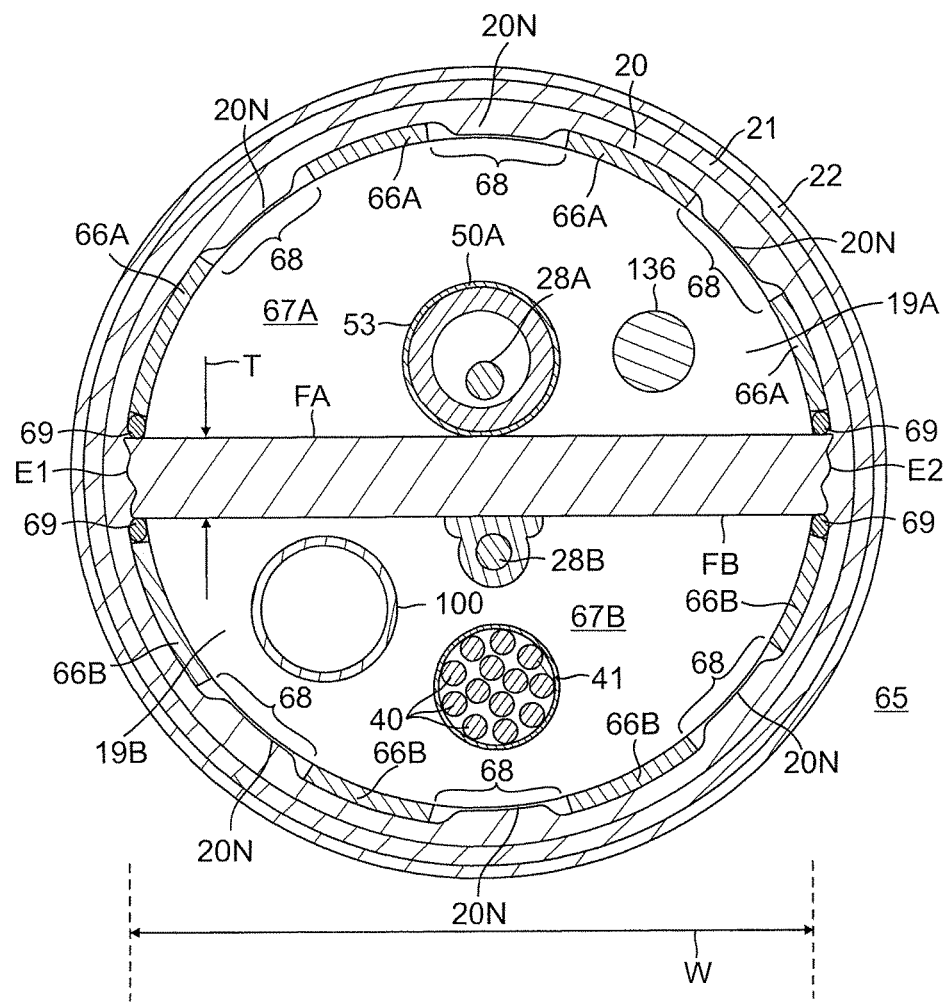
FIG. 2A is an end cross-sectional view of the transition section of FIG. 2, taken along line A-A.

With reference to FIGS. 2 and 2A, the catheter body 12 is an elongated tubular structure comprising a single, central or axial lumen 18. The catheter body 12 is flexible, i.e., bendable, but substantially non-compressible along its length. The catheter body 12 may be of any suitable construction and made of any suitable materials. In one embodiment, the catheter body 12 is multi-layered comprising at least an inner coat or layer 20, and an outer coat or layer 22 with an imbedded braided mesh 21 of stainless steel or the like to increase torsional stiffness of the catheter body 12 so that, when the control handle 16 is rotated, the deflectable portion of the catheter 10 rotates in a corresponding manner. The outer diameter of the catheter body 12 is not critical, but is preferably no more than about 8 French. Likewise the thicknesses of the layers 20 and 22 are not critical.

The deflectable section 14 is a shorter tubular structure having a similar construction to the tubular structure of the catheter body 12 except with greater flexibility. In the embodiment of FIGS. 2 and 2A, the deflectable section 14 has a central lumen 19 and a multi-layered construction comprising at least an inner coat or layer 24, and an outer coat or layer 26 with an imbedded braided mesh 25 of stainless steel or the like. The outer diameter of the deflectable section 14 is similar to the catheter body 12, at preferably no more than about 8 French. Suitable materials for the inner layers 20 and outer layer 24 include materials with high heat deflection temperatures so deflection characteristics are not modified by the patient's body temperature.

Suitable materials for the layers of the catheter body 12 and the deflectable section 14 include materials with moderate heat deflection temperatures so stiffness of the deflection section 14 and thus its deflection characteristics are not modified by introduction into the patient's body due to temperature variations. Suitable materials for the inner and outer layers 20 and 22 of the catheter body 12 include Pebax and Pellethane. Materials particularly suitable for both the inner and outer layers 20 and 22 include lower shore hardness plastics ranging from 25-55 D.

Suitable materials for the inner and outer layers 24 and 26 of deflectable section 14 include polyurethane or PEBAX. In one embodiment, the tubular structure 17 of the deflectable section 14 includes an extruded braided structure, with the inner layer 24 having a thickness ranging between about 0.002 inch to 0.003 inch of natural "sticky" 2533-SA-01 PEBAX, then braided with 0.0016 inch diameter, PEN braid (50-80 pies per inch), and the outer layer 26 including extruded PEBAX 5533-SA-01 or 4033-SA-01 PEBAX with about 25% barium sulfate added for radiopacity.

Extending through the length of the deflectable section 14 is an elongated support structure configured as a flat beam or "blade" 30 ("beam" and "blade" used interchangeably herein) with a rectangular cross-section R having a greater width W and a lesser thickness T, as shown in FIG. 2A, defining two opposing rectangular face surfaces FA and FB (or sides, used interchangeably herein) FA and FB that are flat or smooth, and two opposing edge surfaces E1 and E2 that are friction-inducing, e.g., uneven, rough, textured or serrated to provide raised and/or recessed formations along longitudinal edges of the beam 30. The beam 30 may be constructed of any suitable high yield strength material that can be straightened or bent out of its original shape upon exertion of a force and is capable of substantially returning to its original shape upon removal of the force. Suitable materials for the support beam 30 include full hard, cold worked stainless steel alloys (304 or 316 full hard condition), nickel/titanium alloys (nitinol) or phosphor bronze alloys. Nitinol alloys typically comprise about 55% nickel and 45% titanium, but may comprise from about 54% to about 57% nickel with the balance being titanium. A suitable nickel/titanium alloy is nitinol, which has excellent shape memory, together with ductility, strength, corrosion resistance and temperature stability. The beam 30 effectively divides or bisects the central lumen 19 of the deflectable section 14 into two half-spaces 19A and 19B. Components such as lead wires, cables, and tubings can pass through either space without significant interruption or obstruction.

In accordance with a feature of the present invention, the catheter 10 has exceptional torque transmission capability provided by a joint or transition section 65 between the catheter shaft 12 and the deflectable section 14, as shown in FIGS. 3A and 3B. The transition section 65 transfers torsional forces from the control handle 16 to the distal assembly 15 with high fidelity and low hysteresis, to provide a user with a means to accurately place and control the distal assembly 15 within the patient. The transition section 65 includes a pair of opposing elongated brackets 66A, 66B, each with an "open" configuration that when affixed to opposite surfaces of the beam to face each other together forms hollow body with a "closed" configuration that circumferentially surrounds the beam at the joint. The brackets and the body formed thereby bridge the abutting ends of the tubular structures of the catheter body 12 and the deflectable section 14. The brackets, which can be formed by die cutting or acid etching, provide receiving formations, including recesses, or through holes (e.g., circular perforations or punched through-holes 68) arranged in a predetermined pattern. In one embodiment, the pattern includes a plurality of transverse rows, with adjacent rows being offset although it is understood that other alternating or offset patterns would be suitable, as well. In the illustrated embodiment, there are eleven through-holes, with transverse rows R1, R3, R5 and R7, each with two through-holes, and rows R2, R4 and R6 having one through-hole, with adjacent rows offset by a distance equal to about a diameter or width of a perforation. The brackets 66A, 66B can be constructed of the same material as the blade 30 and may be pre-coated with an adhesive for higher bond strength during heat fusion, as described further below.

In the illustrated embodiment, each bracket has a half cylindrical body with a uniform semi-circular or "C" shape cross section along its length and is affixed to a respective side of the blade 30 along its two outer side edges 69, e.g., by resistance spot welding, brazing or laser welding, to face each other and jointly form a full cylindrical body 66 (used interchangeably with the brackets 66A, 66B) generally surrounding the blade 30 at the transition section. The body 66 overlaps the abutting ends of the catheter body 12 and the deflectable section 14. A distal end of the tubular structure 11 of the catheter body 12 is mounted on or slipped over a proximal end of the body 66, and a proximal end of the tubular structure 17 of the deflectable body 14 is mounted on or slipped over a distal end of the body. In that regard, the blade 30 on which the body 66 is affixed has a proximal end that extends a short distance into the distal end of the catheter body 12. As best shown in FIG. 2A, the body 66 defines a central lumen 67 that is divided or bisected by the blade 30 into two cavities 67A and 67B through which components, such as lead wires, cables, etc., can pass. The length of the body 66 ranges between about 5 mm and 12 mm, preferably between about 6.5 mm and 10 mm.

With reference to FIG. 2, in assembling the transition section 65, distal end 12D of the catheter shaft 12 is slid onto the proximal end of the cylindrical body 66 with proximal end 30P of the blade 30 extending a short distance into the central lumen 18. A proximal end 14P of the deflectable section 14 is slid onto the distal end of the cylindrical body 66 with the blade (and its deflection components) extending through the central lumen 19 toward the distal end of the section 14. Accordingly, the distal end 14D of the deflectable section 14 and the proximal end 12P of the catheter shaft 12 extend over the body 66 from opposite directions such that they abut each other at or near a mid-location along the length of the body 66. The inner coatings 20 and 24, if not also the outer coatings 22 and 26, are then fused to the body 66, with application of sufficient heat and pressure so as to melt, migrate and/or flow to form interlocking nodes 20N and 24N into the perforations 68. This fusion creates a very strong interlocking bond between the catheter shaft 12 and the deflectable section 14. The nodes increase the axial load capacity to the joint. In fact, the resulting torque transmission bond joint can be stronger in torsion and in tensile force loading than the braided catheter shaft 12 and deflectable section 14 that are bonded to it.

To facilitate the application of heat and pressure to the transition section 65, a protective heat-shrink tubing 70, e.g., fluorinated ethylene propylene (FEP) or polyethylene terephthalate (PET) is placed over the transition section to form a tube assembly, and shrunken ("recovered") over the transition section (e.g., by a heat gun or oven) to apply inward pressure against the body 66. The tube assembly is then placed in a two-piece heat fusing die head (not shown) for heating to melt ("reflow") the inner layers 20 and 24 of the tubular structures 11 and 17 of the catheter body 12 and deflectable section 14 to form the interlocking nodes 20N and 24N. The tube assembly is then cooled. The heat shrink tubing 70 can be used as a process aid to prevent the melted layers from contacting the heated die and create a uniform transition between the mating tubular bodies of the catheter body 12 and deflectable section 14. Thus, the shrink tubing 70 is removed from the transition section 65 after the fusing process.

The heat fusing die head utilizes a highly accurate fusing die height measurement indicator (LVDT) to sense fusing die head movement during the heating/fusing process. Since the construction materials of the coatings of the shaft 12 and the deflectable section 14 may include extruded raw thermoplastic polymers with a wide range of heat histories (±25° F.) between material lots, monitoring the softening of the polymers and the resultant die head movement is another means besides temperature measurement to achieve process control while reducing the influence of polymer heat history during the heating/fusing process. Moreover, the transition section can be created in minimal duration (e.g., less than about 60 seconds) using a thermal fusing machine that is water-cooled to provide fast cycle times. The transition section is advantageously homogenous and seamless. The structure of the transition section is nondiversified once heat-pressure fuse operation is completed.

Figure 4:
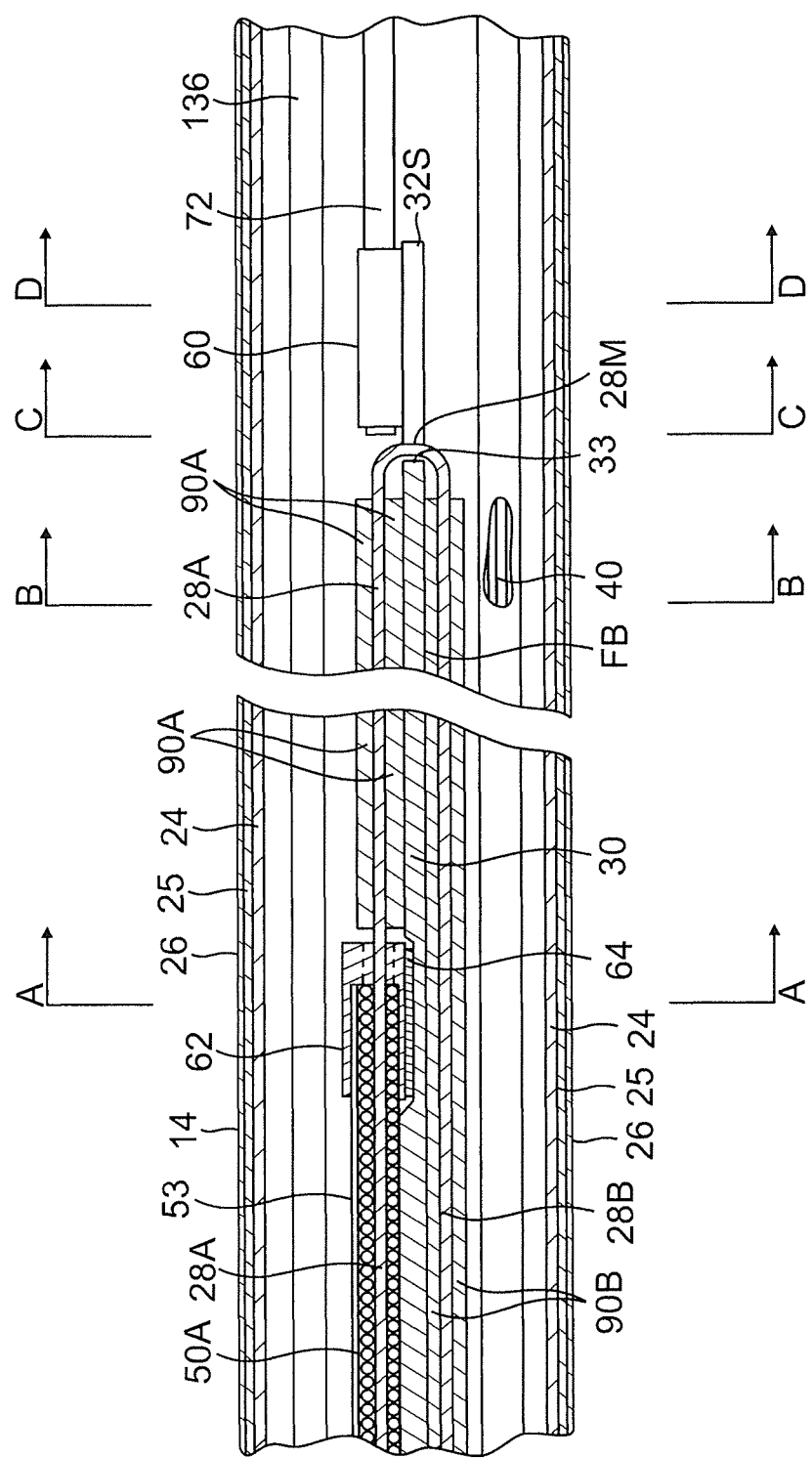
FIG. 4 is a side cross-sectional view of a portion of a deflectable section, including a distal end of a deflection beam, in accordance with an embodiment of the present invention.
Figure 4A:
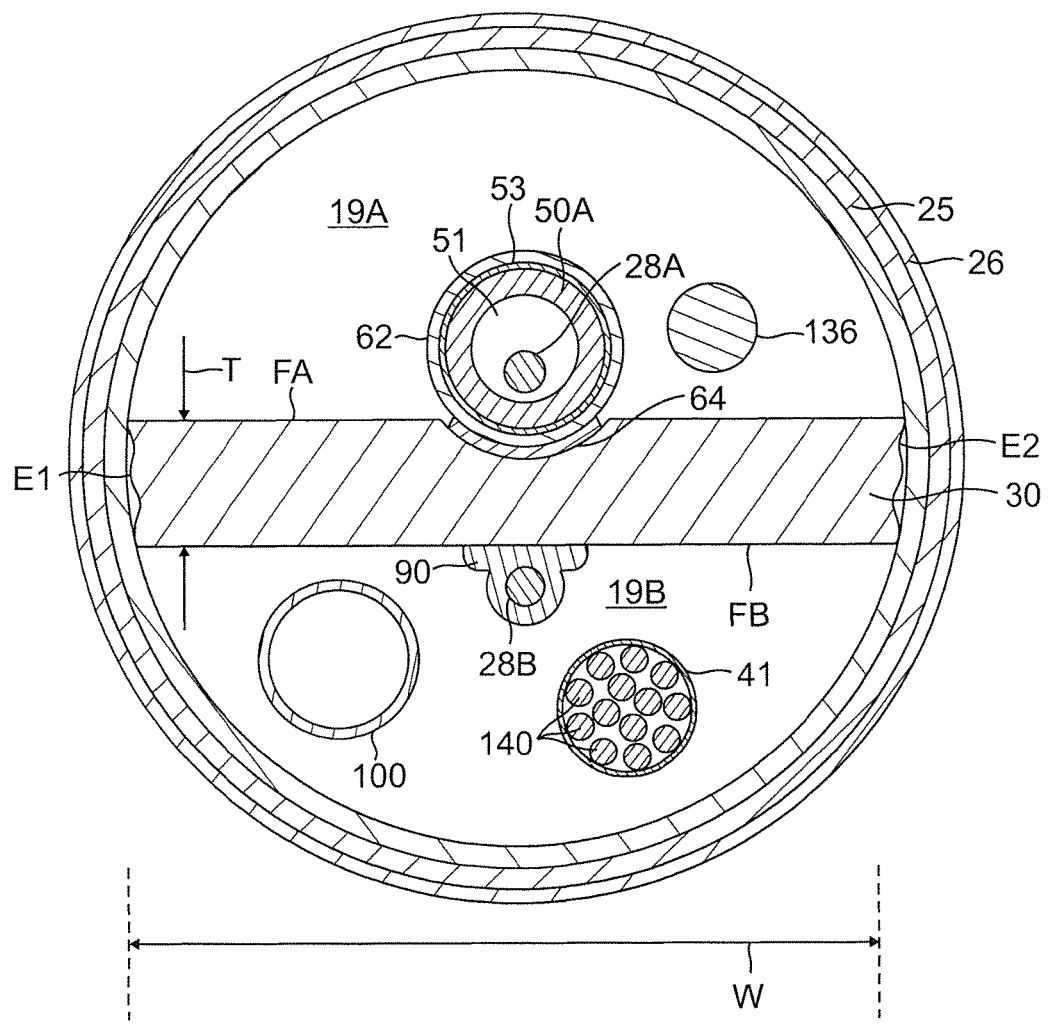
FIG. 4A is an end cross-sectional view of the deflectable section of FIG. 4, taken along line A-A.
Figure 4B:
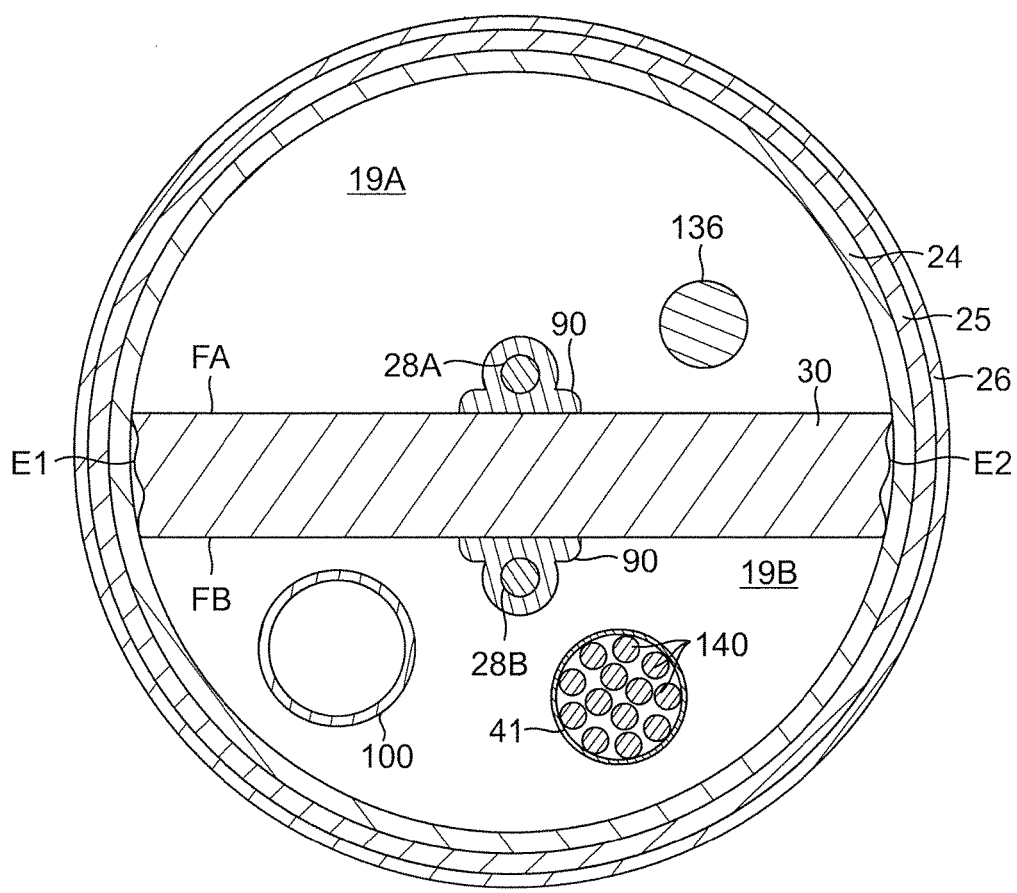
FIG. 4B is an end cross-sectional view of the deflectable section of FIG. 4, taken along line B-B.
Figure 4C:
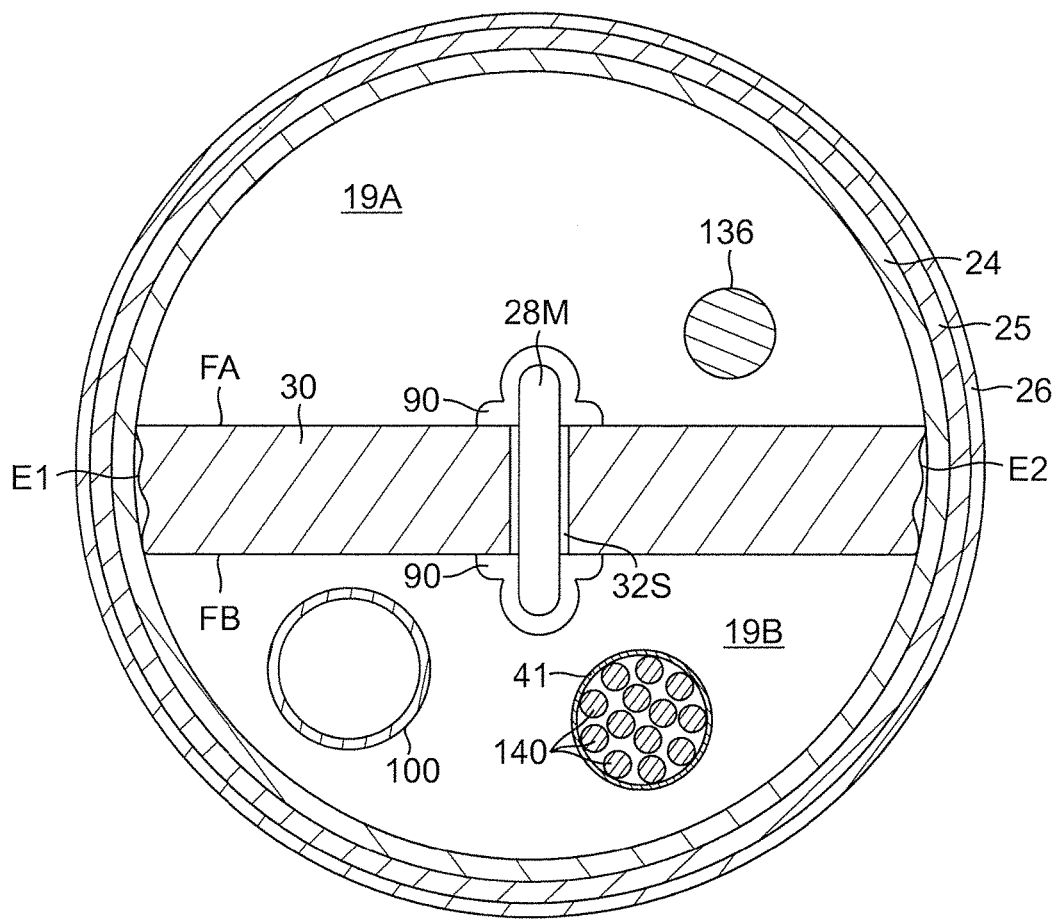
FIG. 4C is an end cross-sectional view of the deflectable section of FIG. 4, taken along line C-C.
Figure 4D:
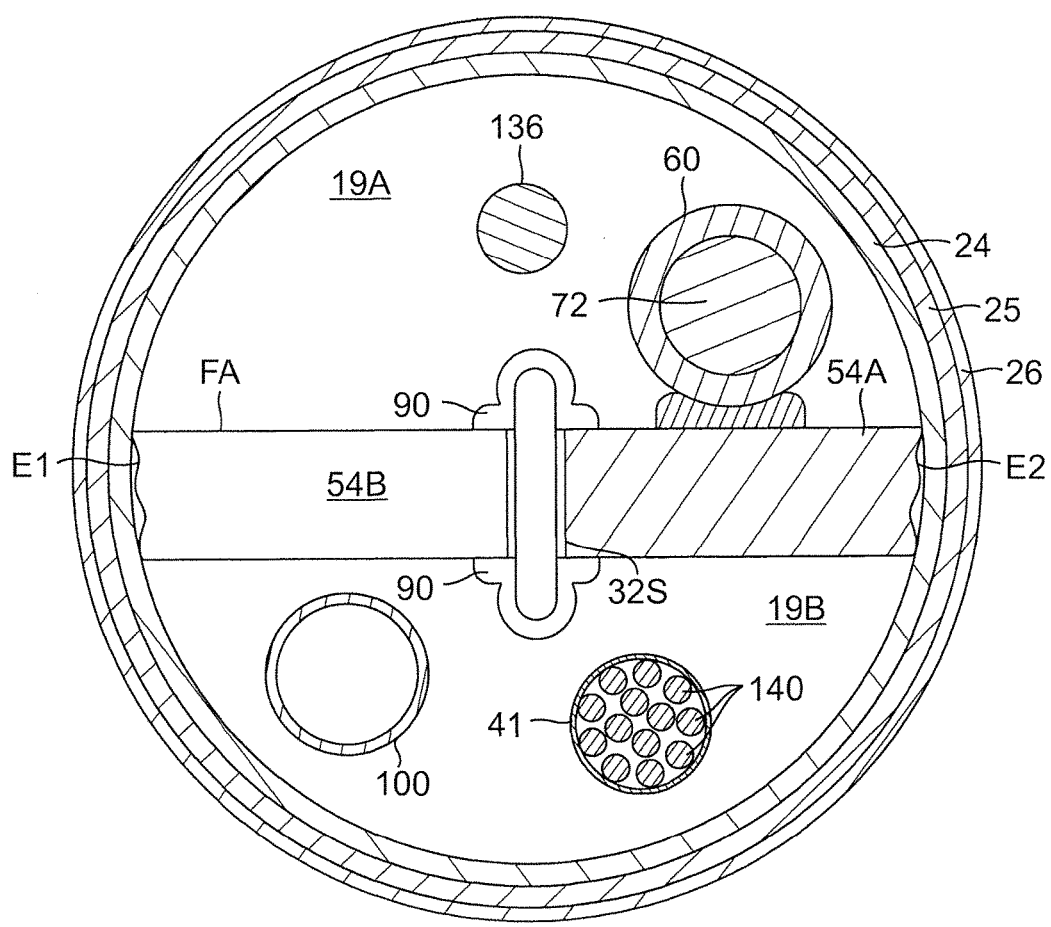
FIG. 4D is an end cross-sectional view of the deflectable section of FIG. 4, taken along line D-D.
Figure 5A:
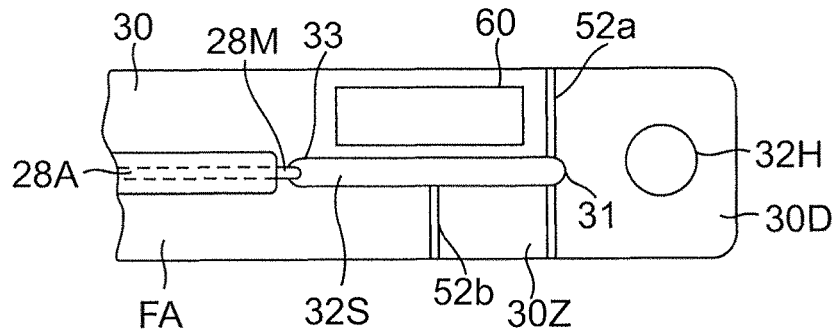
FIG. 5A is a top plan view of a distal end of a deflection beam, in accordance with one embodiment of the present invention.
Figure 5B:
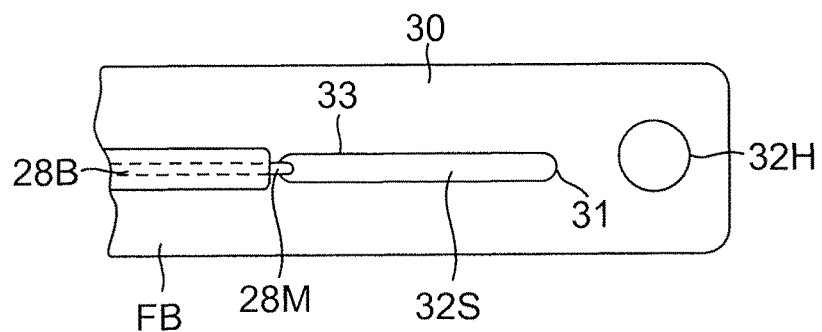
FIG. 5B is a bottom plan view of the distal end of the deflection beam of FIG. 5A.
Figure 5C:
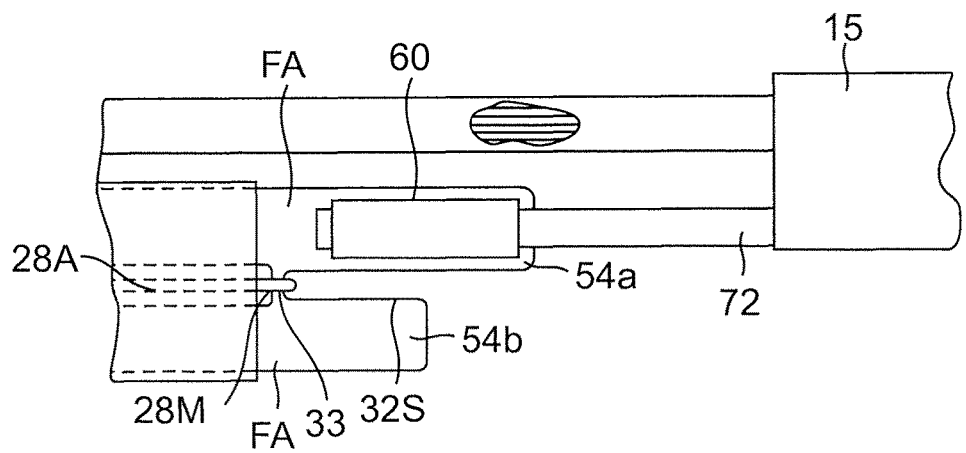
FIG. 5C is a top plan view of the distal end of the deflection of FIG. 5A, with a portion removed, as assembled with a support member of a distal assembly, in accordance with one embodiment of the present invention.

In accordance with a feature of the present invention, the catheter 10 provides bi-directional deflection with a single continuous puller wire 28 that advantageously requires less actuation force by a user and imposes less shear stress on the puller wire. Similar to conventional bi-directional catheters that use a pair of puller wires whose proximal ends are anchored in the control handle, proximal ends of the single continuous puller wire 28 are anchored in the control handle 16. However, the puller wire 28 bends upon itself to form a portion 28M with a U-bend (about 180 degrees) at or near a midpoint along its length, with the U-bend being the distal-most portion of the puller wire in the catheter. As shown in FIG. 4, the U-bend mid-portion 28M divides the puller wire into two main proximal segments 28A and 28B of generally equal length, each with a proximal end that is anchored in the control handle 16. With reference to FIGS. 5A, 5B and 5C, to anchor the U-bend portion 28M at a distal location on the catheter, a distal end of the blade 30 has a receiving formation 32 e.g., either an on-axis slit 32S or an on-axis through hole 32H which securely receives the midportion 28M so that each long portion 28A and 28B extends centrally alongside a respective face surface FA, FB of the blade 30. This arrangement advantageously avoids the use of conventional T-bars, crimp type connections, soldering or welding as a means to attach the puller wire to the blade 30. Because the puller wire is not rigidly attached to the blade 30, this arrangement provides smooth bi-directional steering.

As illustrated in FIGS. 5A and 5B, the distal end of the blade 30 has an original configuration prior to assembly of the catheter and attachment of the puller wire 28 which includes an elongated longitudinal closed slit 32S with a distal end 31 and a proximal end 33. The slit 32S is disposed immediately proximal of a distal end portion 30D of the blade 30. The through-hole 32H is disposed in the distal end portion 30D. The U-bend mid portion 28M of the puller wire may be inserted and hooked through the hole 32H, or alternatively in the slit 32S at its proximal end 33. In the latter regard, the slit 32S is adapted into an open configuration from a closed configuration for receiving the U-bend mid-portion 28M when the distal end portion 30D of the blade is detached by a user bending or cutting along a transverse "pre-cut" groove 52 (FIG. 5A) provided on the face FA of the blade 30 proximal of the hole 32H. In the illustrated embodiment, a first transverse groove 52a is aligned with the distal end 31 of the slot 32 and a second (half width) transverse groove 52b is aligned at or near a midpoint along the length of the slot 32S. Thus, the distal end portion 30D can be readily broken off or otherwise detached from the blade along the groove 52a. For easier access to open slit 32S, another portion 30A can be detached from the blade 30 along the groove 52b, as shown in FIG. 5C.

As shown in FIG. 5C, the slit 32S is generally centered and on-axis with the longitudinal axis of the blade 30 such that the slit divides the blade alongside into two generally equal elongated sections or halves 54a, 54b. On selected section 54a, a hollow tube or ferrule 60 (e.g., of stainless steel) is laser welded to face FA of the section 54a. A proximal end of a support member 72 supporting the distal assembly 15 is inserted and anchored in the tube 60, e.g., by crimping, to create an interference fit between the tube and the support member to transmit torque and tension/compression forces from the blade to the distal assembly. A mechanical crimp process eliminates problematic adhesive bonding that can loosen or fail causing the distal assembly 15 to spin. A servo process with precision force control is sued to detect a defined force slope so that acceptable interference between the support member 72 and the tube 60 is created without damaging the puller wire 28.

Where the deflection blade 30 has equal stiffness on both faces along its longitudinal axis, deflection on either side of the blade has a similar deflection initiation location (or curve generation location) and the catheter provides symmetrical bi-directional deflection. However, in accordance with a feature of the present invention, the blade 30 has a different deflection initiation location on each side, thereby providing nonsymmetrical bi-directional deflection. With reference to FIG. 1, the blade 30 has different and "independent" deflection on each side such that deflection on one side does not influence or affect deflection on the other side. In the embodiment of FIG. 1, side FA of the blade 30 has deflection initiation location A at a distal location, as provided by a lumened stiffener 50A, e.g., a pre-loaded compression coil, affixed to one side of the blade. The compression coil 50A is flexible in elongation but resists compression and thus it provides a deflection initiation location A at or near its distal end. The compression coil has a proximal end generally coterminous with the proximal end of the catheter shaft 12. It extends through the central lumen 18 of the catheter shaft 12. In the deflectable section 14, the compression coil 50A lies on the side FA of the blade 30 along a center longitudinal axis of the blade, as shown in FIGS. 3A and 4. Throughout the catheter shaft 12 and the deflectable section 14, the puller wire segment 28A extends through a central lumen of the compression coil 50A (FIG. 2A). Accordingly, when the blade 30 is deflected toward the side FA, the coil 50A is in compression and behaves as a rigid column, especially when further constrained by a heat shrink tube cover 53, e.g., of thin-walled PET. Thus, deflection on the side FA begins and occurs distal of the compression coil 50A with a deflection initiation location A at or near the distal end of the compression coil.

In contrast, when the blade 30 is deflected toward the side FB opposite of the compression coil 50A, the compression coil is in tension and deflects along with the blade 30 toward side FB along the length of the blade 30. In that regard, a second compression coil is provided for the puller wire segment 50B (FIG. 2). Throughout the catheter shaft 12, the puller wire segment 28B extends through a central lumen of the compression coil 50B. The compression coil 50B has proximal and distal ends that are generally coterminous, respectively, with the proximal and distal ends of the catheter shaft 12. In the illustrated embodiment, the distal end is a short distance proximal of the proximal end of the beam 30. Thus, deflection on the side FB begins and occurs distal of the compression coil 50B with a deflection initiation location B at or near the distal end of the catheter shaft 12.

With this configuration, each side of the blade has a different deflectable working length and two distinct curvatures can be created in the deflectable section 14 using a single continuous puller wire. As illustrated, the side FA of the blade 30 with the compression coil 50 has a tighter or sharper curvature with a smaller defined radius and a more distal deflection initiation location A compared to the opposite side FB of the blade 30 which has a looser, larger and gentler curvature with a greater defined radius and a more proximal deflection initiation location B. Accordingly, the deflectable working length of side FA is shorter than the deflectable working length of side FB.

As shown in FIGS. 3A and 4, a stop, e.g., in the form of a stop tube 62, is provided to affix the distal end of the compression coil 50 to the blade 30. The stop tube 62 has an outer diameter which is generally uniform along the length of the stop tube, and an inner bore 63 to receive at its proximal end the distal end of the compression coil 50 with a slip fit. The inner bore 63 has a larger inner proximal diameter to accommodate the compression coil 50 and a smaller inner distal diameter through which the puller wire 28A passes.

In one embodiment, the larger proximal inner diameter is between about 0.001-0.003 inches larger than the compression coil diameter. The smaller distal inner diameter is between about 0.003-0.006 inches smaller than the compression coil diameter. Where the stop tube 62 has a length L, the length or longitudinal span of the larger proximal inner diameter bore ranges between about 0.6 L to 0.8 L and the length or longitudinal span of the smaller distal inner diameter ranges between about 0.2 to 0.4 L.

The stop tube 62 may be affixed to the blade 30, e.g., by resistance welding, in a location slot or recess 64 formed on the face FA for easy placement and alignment. The recess 64 may be acid etched.

Proximal ends of the portions 28A and 28B are anchored in the control handle 16 and deflection mechanism in the control handle 16 responsive to the actuator 13 manipulated by a user is configured to draw on a selected proximal end of the puller wire along one side of the blade 30 to deflect the catheter with a distinct curvature on that one side. The puller wire 28 may be coated with PTFE or Teflon so the long portions 28A and 28B can slide smoothly inside the protective tubes 36A, 36B when the portions are drawn distally by the deflection mechanism.

As understood by one of ordinary skill in the art, the puller wire 28 is in tension to create a bending moment to deflect the blade 30 in the desired direction. Conventional catheter with a flat blade may use a puller wire with a rectangular cross-section that is welded and tightly constrained to the blade to prevent adhesion failure. While this design may be simple and compact in certain respects, the puller wire is under significant force due because of its close proximity to the blade, which in pure bending requires a substantial bending moment stress during deflection. In contrast, the catheter of the present invention is configured to provide a spacer 90 of a predetermined thickness to separate the puller wire 28 and a neutral bending axis NA of the blade 30 by a predetermined distance so as to lower the force on the puller wire, including the bending moment. Moreover, the catheter 10 includes a puller wire with a round (or at least nonrectangular) cross section to reduce the area moment of inertia, as an otherwise rectangular puller wire with the same cross-sectional area separated from the neutral axis by a comparable spacer would unduly increase the size/diameter of the catheter and the area moment of inertia to result in an unacceptably stiff catheter.

Figure 6A:
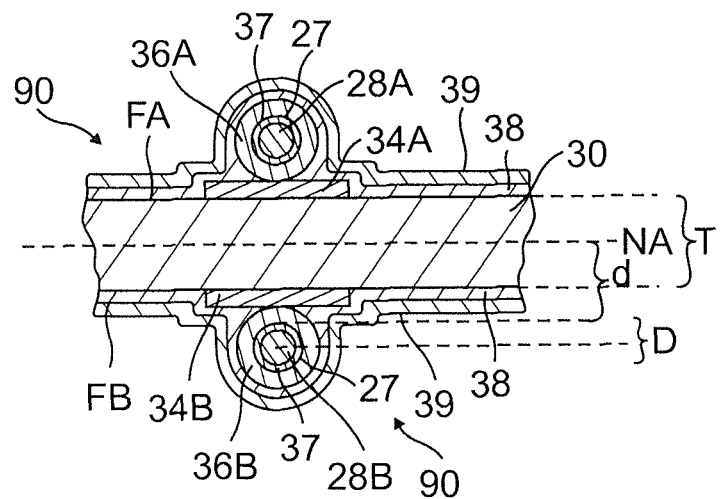
FIG. 6A is an end cross-sectional view of a deflection beam with a spacer on each side, in accordance with one embodiment of the present invention.
Figure 6B:
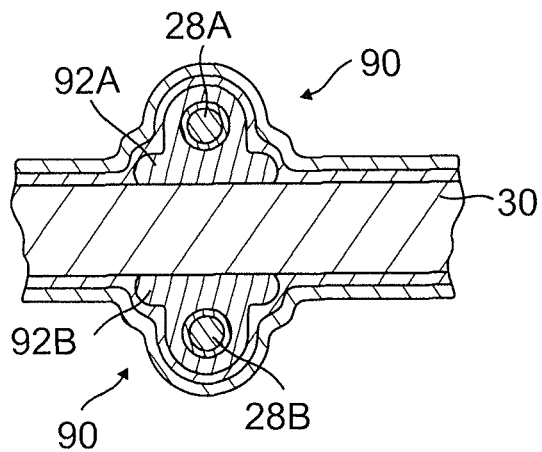
FIG. 6B is an end cross-sectional view of a deflection beam with a spacer on each side, in accordance with another embodiment of the present invention.

In one embodiment as shown in FIG. 6A, the spacer 90A and 90B on each side of the blade 30 includes a first inner adhesive layer 34A, 34B and a wall of a lumened elastomeric puller wire tube 36A, 36B. The adhesive layer may be an ultra high temperature adhesive transfer tape 34A and 34B sold by 3M under the model 100HT. The tube 36A, 36B, which may be constructed of polyimide, is affixed to the respective adhesive layer 34A, 34B and a respective puller wire proximal portion 28A and 28B extends through its lumen 37. An interior surface of the tubing 36 surrounding the puller wire may be coated with PTFE e.g. TEFLON to reduce friction with the puller wire. On side FA, the spacer 90A runs longitudinally from near the receiving formation 32 and the U-bend portion 28M to near a distal end of the stop tube 62. On side FB of the blade 30, the spacer 90B runs generally the entire length of the blade 30. Thus, in the deflectable section 14 and along the blade 30, the puller wire is without the spacer 90 in the U-bend portion 28M and through the compression coil 50. Alternatively, the spacer 90 may include extrusions 92A and 92B surrounding the puller wire as shown in FIG. 6B. The extrusions 92, which may be made of PEEK, has a cross-sectional shape that has a main round or circular portion (to match and surround the round puller wire) and a thin wide elongated base portion with rounded corners that interfaces with the surfaces FA and FB. The rounded corners advantageously reduce material stress concentrations during deflection.

The round puller wire 28 has a diameter D ranging between about 0.007 inch and 0.009 inch, and preferably about 0.008 inch. The blade 30 has a thickness T of about 0.004 inch and 0.007 inch, and preferably between about 0.005 inch and 0.006 inch. The puller wire and the neutral axis are separated by a distance d, ranging between about 0.008 inch and 0.025 inch, and preferably between about 0.10 inch and 0.015 inch.

In the embodiment of FIGS. 6A and 6B, the diameter D is 0.008 inch, the blade thickness is 0.005 inch and the distance d is 0.0105 inch, leaving a separation d between the puller wire and the adjacent surface of the blade (and a spacer thickness) of 0.004 inch. Compared to a rectangular puller wire with the same cross sectional area (e.g., 0.010 inch×0.005 inch), the puller wire force can be reduced by at least half to create the same bending moment to deflect the blade. The stress force on the puller wire can also be less than half.

To constrain and secure the puller wire 28 on the blade 30 and as an additional means to prevent adhesive failure and detachment, at least a first inner heat shrink tubing 38 is placed on the blade 30, covering and surrounding the spacers on both sides of the blade (with the puller wire portions 28A, 28B trained through the spacers). In the illustrated embodiment of FIGS. 6A and 6B, the first inner heat shrink tubing 38 is followed by a second outer heat shrink tubing 40 that is placed over the assembly to surround and seal the components and the first heat shrink tubing 38. The first heat shrink tubing 38 may constructed of high temperature resistant polyester (PET) or FEP. The second heat shrink tubing 40 may be constructed of extruded natural PEBAX or natural Pellethane. The uneven longitudinal edges E1 and E2 of the blade 30 help grasp and secure the first and second heat shrink tubings so they do not migrate or slip during deflection.

In the illustrated embodiment of FIG. 1, the distal assembly 15 comprises a generally straight proximal region and a generally circular main region having at least one loop circling about 360 degrees, if not two loops circling about 720 degrees. The proximal region 98 is mounted on the deflectable section 14 and the main region 99 carries a plurality of electrodes for mapping and/or ablation. With reference to FIG. 4, 5, the distal assembly 15 includes the shape memory support member 72, lead wires 140 for the electrodes carried on the distal assembly 15, and a cover extending the length of the distal assembly. The lead wires 140 attached to the electrodes on the distal assembly 15 extend through a nonconductive sheath 41 which extends from the distal assembly through the lumen half 19B of the deflectable section 14, through the cavity half 67B of the transition section 65, through the lumen 18 of the catheter shaft 12, and into the control handle 16.

An electromagnetic position sensor (not shown) is mounted in or near the distal assembly 15, e.g., in the distal end of the deflectable section 14. A sensor cable 136 extends from the sensor into the half lumen 19A of the deflectable section 14, the cavity half 67B of the transition section 65, the central lumen 18 of the catheter body 12 and into the control handle 16 where it terminates in a suitable connector (not shown).

If irrigation at or near the distal assembly 15 is desired, an irrigation tubing 100 is provided to pass fluid from a source (not shown) along the catheter. In the illustrated embodiment, the irrigation tubing 100 extends through the control handle 16, the central lumen 18 of the catheter body 12, and the half space 19B of the deflectable section 14.

In use, a suitable guiding sheath is inserted into the patient with its distal end positioned at a desired location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with an embodiment of the present invention is fed through the guiding sheath until its distal end extends out of the distal end of the guiding sheath. As the catheter is fed through the guiding sheath, the distal assembly 15 is straightened to fit through the sheath. Once the distal end of the catheter is positioned at the desired location, the guiding sheath is pulled proximally, allowing the deflectable section 14 and distal assembly 15 to extend outside the sheath, and the distal assembly 17 returns to its original shape due to its shape-memory.

The user manipulating the actuator 13 on the control handle 16 actuates deflection mechanism inside the control handle to draw on a selected puller wire proximal portion 28A or 28B. Where distal portion 28A is selected, the deflection curvature DA on one side of the deflection beam 30 initiates at or near the distal end of the compression coil A for a distinct curvature from the deflection curvature DB on the other side of the deflection beam 30. The force and stress on the puller wire 38 are minimized by the flat deflection beam and puller wire assembly which tightly constrains the puller wire (with a round cross-section) to the beam with a predetermined separation distance from the neutral bending axis of the deflection beam. The user may then rotate the generally circular main region 99 of the distal assembly 15 by rotating the control handle 16 which transfers torque to the catheter body 12 and the deflectable section 14 through the transition section 65 therebetween by means of the half cylindrical members 66A and 66B to which the tubular structures of the catheter body 12 and the deflectable section 14 are bonded by means of interlocking that melt into the perforations 68 in the members 66A and 66B under heat fusion.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller wire advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
   an elongated catheter body comprising a first tubular structure having first central lumen, a distal end and a proximal end, the first tubular structure having a layer of thermoplastic material;
   a deflectable section having a second tubular structure having a second central lumen, and a proximal end that is distal of the proximal end of the catheter body, the second tubular structure having a layer of thermoplastic material;
   a joint between the distal end of the first tubular structure and the proximal end of the second tubular structure, the joint including a first half cylindrical bracket with two first edges and a second half cylindrical bracket with two second edges, each bracket having at least one receiving formation;
   a beam having a generally rectangular cross-section with first and second opposing surfaces, at least a portion of the beam extending through the joint; and
   wherein the two first edges are affixed to the first surface of the beam and the two second edges are affixed to the second surface of the beam such that the first and second brackets form a hollow body surrounding the portion of the beam, a distal portion of the hollow body being covered by the layer of thermoplastic material of the second tubular structure, a proximal portion of the hollow body being covered by the layer of thermoplastic material of the first tubular structure, the layers of thermoplastic materials of the first and second tubular structures each having at least one node extending into the receiving formation.

2. The catheter of claim 1, wherein an outer surface of each of the first half cylindrical bracket and the second half cylindrical bracket is coated with an adhesive adapted to bond with the layers of thermoplastic materials.

3. The catheter of claim 1, wherein each receiving formation has a circular cross-section.

4. The catheter of claim 1, wherein the receiving formations of each bracket are arranged in a predetermined offset pattern.

5. The catheter of claim 1, wherein the first edges of the first half cylindrical bracket are affixed to outer edges of the first surface of the beam and the second edges of the second half cylindrical bracket are affixed to outer edges of the second surface of the beam.

6. The catheter of claim 1, wherein the beam divides the hollow body longitudinally.

7. The catheter of claim 1, wherein each layer of thermoplastic material is covered by a braided mesh.

8. The catheter of claim 7, wherein each layer of braided mesh is covered by an elastomeric material.

9. The catheter of claim 1, wherein each bracket is made of a high strength spring material.

10. The catheter of claim 9, wherein the high strength spring material is selected from the group consisting of stainless steel, nitinol and phosphor bronze.

11. The catheter of claim 1, further comprising a puller wire having first and second main sections and a U-bend section therebetween, the U-bend section anchored to a distal end of the beam.

12. The catheter of claim 11, wherein the beam bisects the hollow body to form a first lumen half and a second lumen half, the first main puller wire section extending through the first lumen half and through the first central lumen of the catheter body, and the second main puller wire section extending through the second lumen half and through the first central lumen of the catheter body.

13. The catheter of claim 12, further comprising a first compression coil having a proximal end at or near the proximal end of the catheter body and a distal end distal of the joint, the first compression coil having a coil lumen through which a portion of the first main puller wire section extends.

14. The catheter of claim 13, wherein the first compression coil extends through the first central lumen of the catheter body and through the first lumen half.

15. The catheter of claim 13, further comprising a stop having a bore configured to receive a distal end of the first compression coil with the first main puller wire section therein extending through the bore, the stop configured to affix the first compression coil to the first surface of the beam.

16. The catheter of claim 13, further comprising a heat shrink tube surrounding the first compression coil.

17. The catheter of claim 11, further comprising at least one spacer extending axially on at least one surface of the beam configured to provide a predetermined separation distance between the respective puller wire section and the at least one surface of the beam.

18. The catheter of claim 17, further comprising at least one heat shrink tube constraining the spacer and its puller wire section to the beam.

19. The catheter of claim 17, wherein the at least one spacer includes an extrusion.

20. The catheter of claim 17, wherein the at least one spacer comprises an adhesive layer and a tubing.

* * * * *